(12) United States Patent
Devonec

(10) Patent No.: US 8,070,825 B2
(45) Date of Patent: Dec. 6, 2011

(54) PROSTATIC STENT AND A DETACHABLE CATHETER APPARATUS COMPRISING THE SAME

(76) Inventor: Marian Devonec, Miribel (FR)

( * ) Notice: Subject to any disclaimer, the term of this patent is extended or adjusted under 35 U.S.C. 154(b) by 458 days.

(21) Appl. No.: 11/920,974

(22) PCT Filed: May 23, 2006

(86) PCT No.: PCT/IB2006/001343
§ 371 (c)(1),
(2), (4) Date: Jan. 23, 2008

(87) PCT Pub. No.: WO2006/126060
PCT Pub. Date: Nov. 30, 2006

(65) Prior Publication Data
US 2008/0234832 A1    Sep. 25, 2008

Related U.S. Application Data

(60) Provisional application No. 60/683,298, filed on May 23, 2005.

(51) Int. Cl.
*A61F 2/82*    (2006.01)

(52) U.S. Cl. .......................................... 623/23.7; 600/29

(58) Field of Classification Search ........ 623/1.15–1.17, 623/23.7; 606/192, 198
See application file for complete search history.

(56) References Cited

U.S. PATENT DOCUMENTS

| | | | |
|---|---|---|---|
| 5,766,209 A | 6/1998 | Devonec | |
| 5,876,417 A | 3/1999 | Devonec et al. | |
| 6,238,368 B1 | 5/2001 | Devonec | |
| 6,290,666 B1 | 9/2001 | Devonec | |
| 2001/0041883 A1 | 11/2001 | Devonec | |
| 2002/0107540 A1* | 8/2002 | Whalen et al. | 606/192 |
| 2003/0060894 A1* | 3/2003 | Dua et al. | 623/23.68 |
| 2003/0208183 A1 | 11/2003 | Whalen et al. | |

FOREIGN PATENT DOCUMENTS

| | | |
|---|---|---|
| WO | WO 94/18907 A1 | 9/1994 |
| WO | WO 96/02210 A1 | 2/1996 |
| WO | WO 03/011179 A2 | 2/2003 |

* cited by examiner

*Primary Examiner* — Suzette J Gherbi
(74) *Attorney, Agent, or Firm* — Oliff & Berridge, PLC

(57) ABSTRACT

The present invention is an endo-prostatic stent and a detachable catheter apparatus including the same, allowing the correct positioning of the stent using tactile feed-back of the operator during insertion i.e. without the need for any imaging means like endoscopy or sonography.

15 Claims, 3 Drawing Sheets

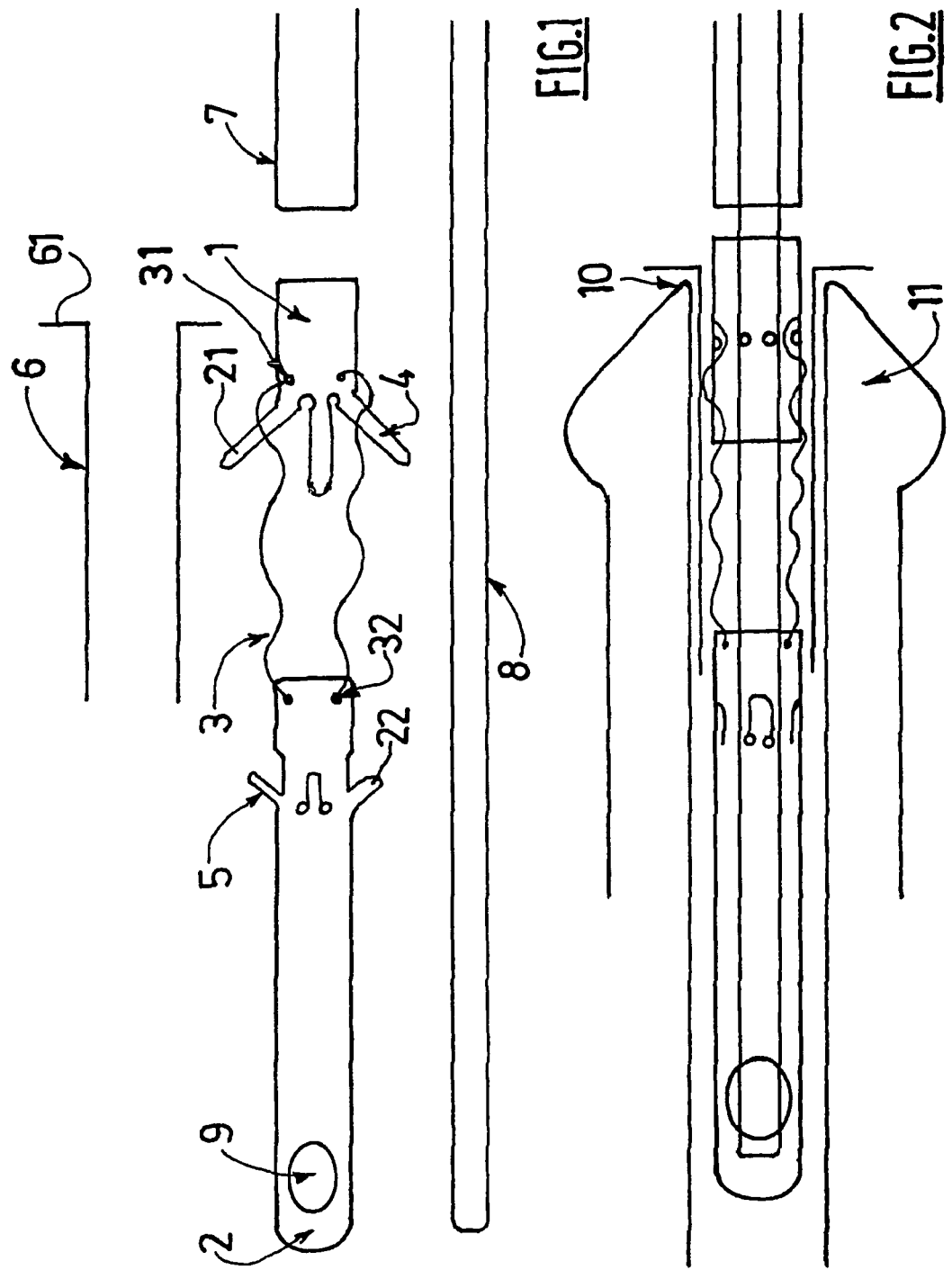

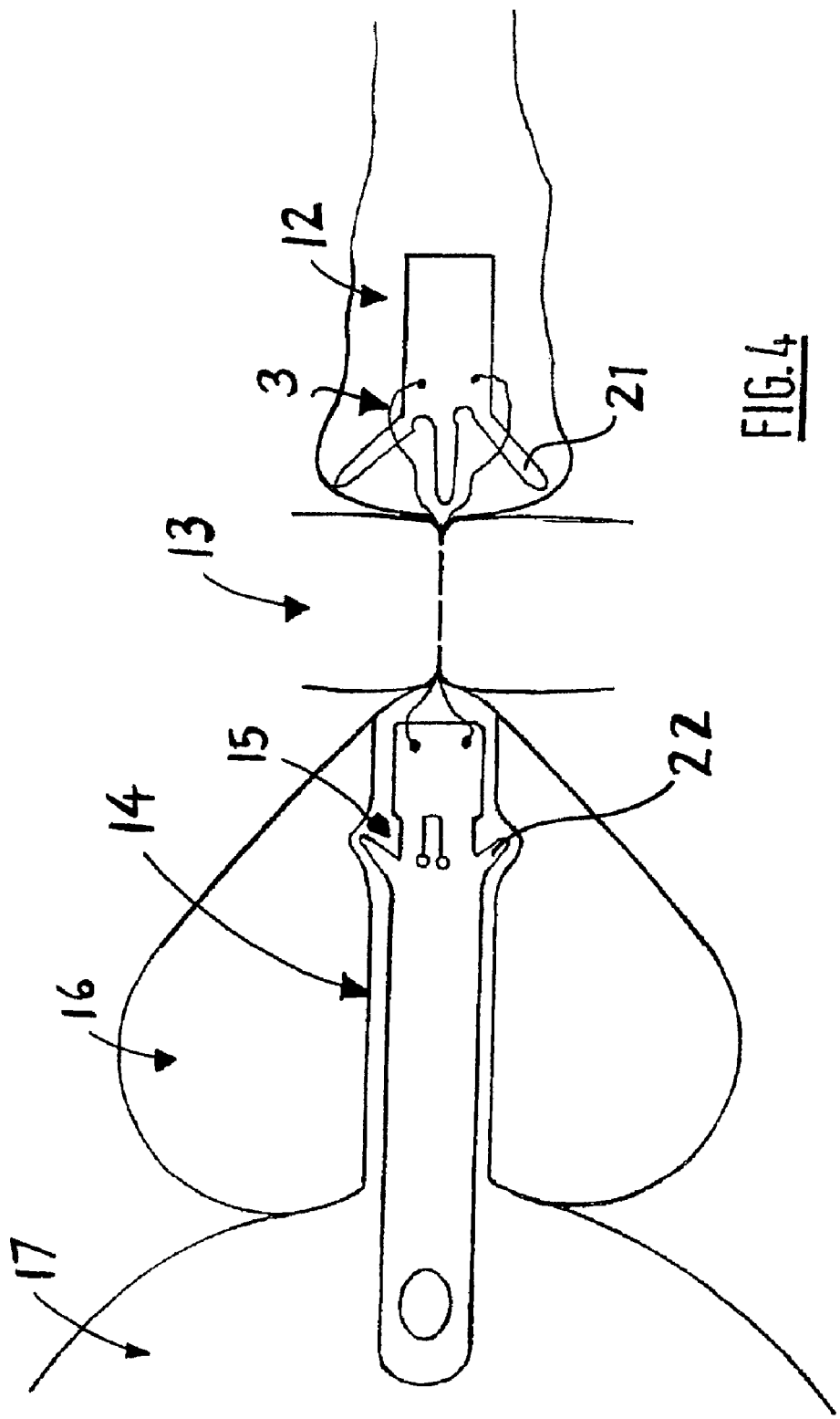

PROSTATIC STENT AND A DETACHABLE CATHETER APPARATUS COMPRISING THE SAME

Figure 3:
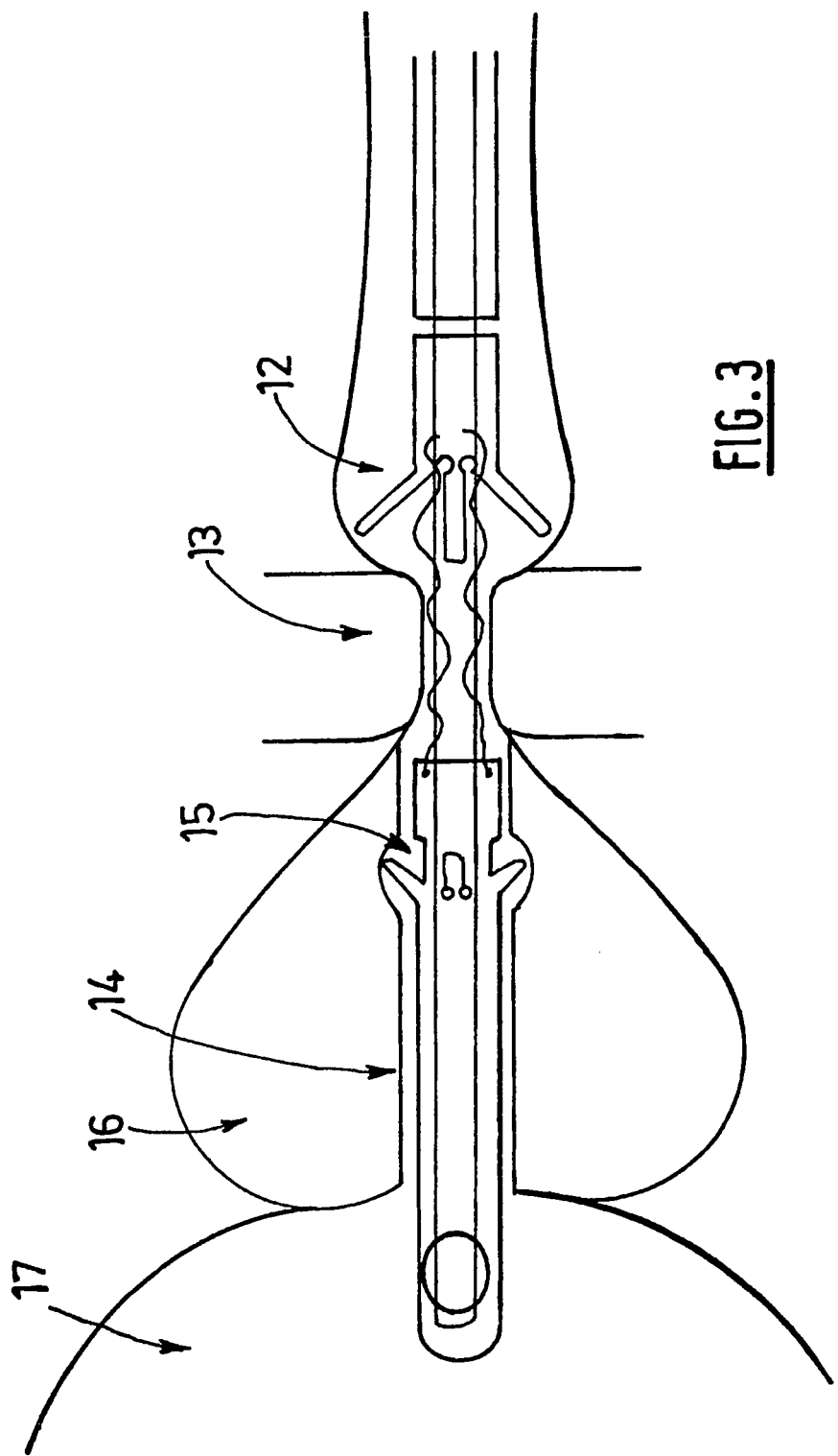

The present invention concerns a prostatic stent and a detachable catheter apparatus comprising the same, as generally described in U.S. Pat. No. 5,876,417, the content of which is hereby incorporated by reference.

In U.S. Pat. No. 5,876,417, a prostatic stent consisting of a tube assembly has been described. This tube assembly comprises a distal tube section having a closed distal end and a proximal opened part, said distal end including at least one orifice to enable urine from the bladder to enter the distal tube section and to flow into and through the distal tube section, across connection means and through said sphincter; a proximal tube section having a distal part and a proximal end; and connection means connecting the proximal part of said distal tube section and the distal part of said proximal tube section together.

According to U.S. Pat. No. 5,876,417, so as to position and insert said stent through the urethra having a sphincter of a male living being to convey urine, the tube assembly of the prostatic stent makes part of a detachable catheter apparatus extending along a longitudinal axis, said detachable catheter comprising:

a) a tube assembly being the prostatic stent, b) an insertion device slidably receivable into said tube assembly, said insertion device comprising an elongated inner alignment rod having a contact distal end and an insertion proximal end portion, said rod being longitudinally sized to extend into the tube assembly wherein the contact distal end contacts the closed distal end of said distal tube section while the proximal end portion projects outwardly from said tube assembly; and an outer pusher tube having a bore longitudinally therethrough and sized to slidably receive said alignment rod, c) an expandable member disposed circumferentially about and longitudinally along the distal part of said proximal tube section, and operative to move between an expanded state wherein the expandable member expands radially outwardly and abuts against said sphincter and a collapsed state wherein the expandable member collapses, d) expansion and/or collapse controlling means of said expandable member.

U.S. Pat. No. 5,876,417 shows two distinct embodiments for the detachable catheter apparatus according to one embodiment, the expandable member is an inflatable balloon localized on the outer surface of the proximal tube section according to a second embodiment, the expandable member is a Malecot arrangement comprising tongues, each tongue being foldable between two positions, namely a first position folded outwards at its centre and an unfolded position in which it is included in the wall of the proximal tube section.

Both embodiments are insufficient to reproduce regularly correct positioning of the stent in the prostatic urethra. Often, the lower tube section of the stent was pushed above the sphincter. The abutment of the Malecot or of the inflated balloon against the external sphincter was not clearly perceived by the operator. After removal, the stent had to be reinserted and positioned under the control of endoscopy or transrectal ultrasonography. Upwards and downwards migration of the urethral stent were observed.

One object of the present invention is to propose an endo-prostatic stent and a detachable catheter apparatus including the same, to allow the correct positioning of the stent using tactile feed-back of the operator during insertion i.e. without the need for any imaging means like endoscopy or sonography.

Another object of the present invention is to decrease the risk of migration of the endo-prostatic stent, once inserted in the urethra and the bladder.

According to the present invention, said expandable member disposed on said proximal tube section is arranged to abut permanently in said expanded state against said sphincter and to oppose any upward movement in said urethra of said catheter apparatus, and, optionally said catheter apparatus comprises another expandable member disposed circumferentially about and longitudinally along the proximal part of said distal tube section, said another expandable member being arranged to be self working between a collapsed state, when said catheter apparatus moves upwards in said urethra towards the bladder, and an expanded state permitted by said urethra and opposing to any downward movement of said catheter apparatus.

Preferably, said distal part of said proximal tube section consists of said expandable member which comprises flexible tongues distributed about said proximal tube section, each of said tongues being arranged to be elastically biased towards a radial and outward position, and said expansion and/or collapse controlling means comprise a sheath adapted to enclose said distal part of said proximal tube section and constrain all tongues in a collapsed position lying in the longitudinal direction of said catheter apparatus; as an example, in said radial and outward position, each tongue extends obliquely with respect to the longitudinal axis towards the distal end of said catheter apparatus.

Preferably, said another expandable member comprises flexible tongues distributed about said distal tube section, each of said tongues being arranged to be elastically biased towards a radial and outward position; as an example, in said radial and outward position, each tongue extends obliquely with respect to the longitudinal axis towards the proximal end of said catheter apparatus.

According to one embodiment of the present invention, said connecting means of said tube assembly connect a proximal end of said distal tube section adjacent to said another expandable member, and a distal portion of said proximal tube section adjacent to said expandable member; as an example said connecting means comprises threads distributed about the longitudinal axis of said catheter apparatus, attached on opposite ends respectively to said proximal end of said distal tube and said distal portion of said proximal tube section.

Thanks to the invention, correct positioning of the urethra stent is obtained by the tactile feedback of the abutment of the expandable member of the proximal tube section against the urinary sphincter. And where another expandable member is disposed on said distal tube section, migration of the stent In any direction (upward and/or downward) is prevented.

The present invention is now described with reference to annexed drawing wherein:

FIG. 1 is a schematical elevation view of a detachable catheter apparatus according to the present invention, including a prostatic stent still according to the present invention.

FIG. 2, still in a schematical manner, shows the insertion of an invention prostatic stent through the urethral meatus, with a detachable catheter apparatus according to the present invention.

FIG. 3, still in schematical manner, shows the insertion of a detachable catheter apparatus according to the present invention, during its insertion into its final position in the urethra and bladder. This figure shows also a schematic representation of the anatomy of the urinary system of a male living being.

FIG. 4, still in a schematical manner, shows the invention prostatic stent in its final position in the urethra and bladder, once the other parts of the detachable catheter apparatus have been successively extracted from the urethra.

LEGENDS FOR FIGURES

1—Proximal tube section
2—Distal tube section
3—Flexible connecting means
4—Expandable member of the proximal tube section
5—Expandable member (another) of the distal tube section
6—Outer sheath
61—Hollow plate of the outer sheath
7—Pusher tube
8—Rod (or stylet)
9—Orifice for urine drainage
10—Meatus of the urethra
11—Penis glands
12—Bulbous urethra
13—Sphincter
14—Prostatic urethra
15—Veru montanum
16—Prostate
17—Bladder
21—Tongues of the half-Malecot of the proximal tube section
22—Tongues of the half-Malecot of the distal tube section
31—Point of attachment of the flexible connecting means 3 on the distal tube section 1,
32—Point of attachment of the flexible connecting means 3 on the proximal tube section 2, As shown in FIG. 1, the invention prostatic stent is made of a tube assembly comprising a proximal tube section 1 and a distal tube section 2 linked by a flexible connecting means 3.

The proximal tube section is characterized by two parts:
a proximal end (the part on the opposite side of the sphincter) has a tubular shape;
a distal part 4 (the part on the side of the sphincter) has a half Malecot design, i.e. with tongues 21.

Said distal part has a tubular shape when tongues 21 are flattened inside an outer sheath 6 gliding along the tube assembly. Same distal part has an umbrella shape when the tongues 21 are spread, as soon as the outer sheath 6 glides outside and allows spreading of the tongues. The degree of their opening adapts automatically to the variable diameter of the urethra during progression of the stent inside the urethra lumen. Maximum opening is observed at the level of the bulbous urethra 12, where urethra diameter is the largest, just below the urinary sphincter. Once the stent is in correct position the opened tongues abut against the lower side of the sphincter preventing from upward migration.

The distal tube section 2 has another expandable member 5 with a half part Malecot design. The latter differs from the one of the proximal tube section 1 in that:
it is not located at one end but distant from it,
its maximum outer diameter, when fully spread, is smaller since adapted to the section of the prostatic urethra at the veru montanum 15,
the orientation of the free tips of the tongues 22 is the opposite of the one of the tongues 21 of the half-Malecot of the proximal tube section, so that the tips of each half-Malecot look at each other. The tongues of the half-Malecot of the distal tube section tend to flatten during insertion of the stent, whereas they spread at the level of the veru montanum as soon as the stent is in position. The latter prevent the stent from downward migration.

The distal tube section has two orifices 9 at the level of its distal end to drain urine out of the bladder. The distal end is closed and smooth.

The inner diameter of the proximal and distal tube sections allows the insertion of an elongated inner alignment rod.

The flexible connecting means 3:
attaches to the distal tube section 2 to its proximal end at a point of attachment 32, whereas,
it attaches to the proximal tube section 1 at a point of attachment 31 that is below its half-Malecot portion (expandable member), and not at the level of the tip of the tongues 21, so that the half-Malecot is pouched forwards from its base and not pulled by the tip of its tongues.
allows a maximum distance between the two tube sections equal to the length of the urinary sphincter,
is thin and flexible enough to allow normal functioning of the urinary sphincter 13. A single or several non resorbable sutures, or a sleeve, or the association of suture plus sleeve can be used for the connecting means 3. The sleeve can be permanent or resorbable. In the latter case, permanent connection is assured by one or several non resorbable sutures after the resorption of the sleeve.

The outer sheath 6 is a tube with:
a length allowing to cover the proximal portion of the distal tube section 2 possibly covering the expandable member 5, the distance between the two tube sections when the flexible connecting means, is in its elongated position, and the distal part with the expandable member 4 of the proximal tube section;
an internal diameter close to the one of the external diameter of the stent and outer pusher tube 7. The outer sheath flattens the tongues 21 and 22 of the two tube sections as well as the gap between the two;
a very thin wall, so that the difference in size between the external diameter of the stent and the one of the outer sheath will not be felt during insertion through the meatus of the urethra;
a hollow plate 61 located at its proximal end. This plate abuts against the meatus of the urethra during insertion of the stent.

The pusher tube 7 is a tube with:
a length adapted to the length of the male urethra. The total length of the stent plus the one of the pusher tube is longer than the length of the male urethra,
the outer diameter is the same as the one of the stent,
the internal diameter allows the insertion of the rod 8.

The alignment rod is a flexible cylinder. It allows the alignment of the stent and of the pusher tube. The length of the rod is the sum of the length of the stent plus the one of the pusher tube. The distal end of the rod abuts against the closed or blind distal end of the distal tube section of the stent.

The procedure for inserting a prostatic stent according to the present invention is now described with references to FIG. 2. The stent is delivered with the two tube sections 1 and 2 and the pusher tube 7 mounted on the rod 8, and with the outer sheath 6 mounted on the pusher tube. The tongues 21 and 22 of the two expandable members 4 and 5 are spread. The outer sheath is moved upwards from its position on the pusher tube to the position where the tongues of both tube sections 1 and 2 are flattened.

The operator holds the pusher tube 7 at the level of the junction with the plate 61 of the outer sheath 6 to secure it in the latter position. The stent is inserted in the urethra until the plate 61 of the outer sheath 6 abuts against the meatus.

According to FIG. 2, as the plate of the outer sheath abuts the meatus the pusher tube 7 is inserted through the outer sheath 6.

At this stage (FIG. 3), the pusher tube 7 is inserted through the outer sheath 6 until the distal end of the stent abuts the urinary sphincter 13. The stent is pushed through the sphincter until the tongues 21 of the proximal tube section spread in the bulbous urethra 12 and stop insertion as they bump against the lower side of the sphincter. The stent is In correct position inside the prostate 16; the distal tube section is inside the prostatic urethra 14, the tongues 22 of its proximal part are spread at the level of the veru montanum 15, the connecting means 3 are at the level of the sphincter and the proximal tube section is located in the bulbous urethra with the tongues 21 of the distal part spread below the sphincter. The orifice 9 at the distal end of the distal tube section is inside the bladder 17 for urine drainage.

According to FIG. 3, the stent is in correct position: the tongues of the expandable member 4 of the proximal tube section abut against the lower side of the sphincter, the connecting means is positioned through the sphincter, and the distal tube section is in the prostatic urethra. The tongues of the expandable member of the distal tube section are spread at the level of the veru montanum. The orifice 9 of the distal end of the stent is in the bladder.

The rod 8, the pusher tube 7, and the outer sheath 6 are successively extracted.

The stent stays in place by itself (FIG. 4): prevention of upward migration is assured by the tongues 21 spread inside the bulbous urethra, prevention of downward migration is assured by the tongues 22 spread at the level of the veru montanum. The flexible connection means allows normal functioning of the sphincter.

According to FIG. 4, the rod 8, pusher tube 7 and outer sheath 6 have been successively extracted. The sphincter is closed over the flexible connecting means 3. The tongues of the two expandable members maintain the correct position of the two tube sections of the stent on both sides of the sphincter. Urine can flow through the two tube sections when the sphincter opens up.

The invention claimed is:

1. A detachable catheter apparatus for insertion into a bladder of a male living being through a urethra having a sphincter of said living being to convey urine, said catheter apparatus extending along a longitudinal axis and comprising:
    a) a tube assembly comprising:
        a distal tube section having a closed distal end and a open proximal end, said closed distal end including at least one orifice to enable the urine from the bladder to enter the distal tube section and to flow into and through the distal tube section;
        a proximal tube section having a distal end, a proximal end, and an expandable member being disposed circumferentially about and longitudinally along said distal end of said proximal tube section and being operative to move between:
            an expanded state wherein the expandable member expands radially outwardly and abuts against said sphincter, and
            a collapsed state wherein the expandable member collapses; and
        a connector connecting the open proximal end of said distal tube section and the distal end of said proximal tube section together; said connector being attached to said proximal tube section at a point of attachment located proximal to the expandable member of said proximal tube section and being attached to said distal tube section at a point of attachment located at the open proximal end, said connector having a length of approximately 36 mm,
    b) an insertion device slidably receivable into said tube assembly, said insertion device comprising:
        an elongated inner alignment rod having a contact distal end and an insertion proximal end portion, said rod being longitudinally sized to extend into the tube assembly, wherein the contact distal end contacts the closed distal end of said distal tube section while the insertion proximal end portion projects outwardly from said tube assembly; and
        an outer pusher tube having a bore longitudinally therethrough and sized to slidably receive said alignment rod, and
    c) an expansion and/or collapse controlling means of said expandable member,
    wherein said expandable member disposed on said proximal tube section comprises flexible tongues, each of said tongues being arranged to be elastically biased towards a radial and outward position so that a degree of the tongues opening adapts automatically to a variable diameter of the urethra during progression of the catheter apparatus inside a lumen of the urethra and said tongues being permanently abutted in spread condition against a proximal side of the sphincter once said catheter apparatus is in a correct position in order to oppose any upward movement of said catheter apparatus in said urethra.

2. The catheter apparatus according to claim 1, wherein said expansion and/or collapse controlling means comprises a sheath adapted to enclose said distal end of said proximal tube section and constrain all the tongues in a collapsed position lying in the longitudinal direction of said catheter apparatus.

3. The catheter apparatus according to claim 2, wherein when the tongues are at said radial and outward position, each of the tongues extend obliquely with respect to the longitudinal axis towards a distal end of said catheter apparatus.

4. The catheter apparatus according to claim 1, wherein said connector comprises threads distributed about the longitudinal axis of said catheter apparatus, attached on opposite ends respectively to said open proximal end of said distal tube section and said distal end of said proximal tube section.

5. The catheter apparatus according to claim 1, wherein said catheter apparatus comprises another expandable member disposed circumferentially about and longitudinally along the open proximal end of said distal tube section, said another expandable member being arranged to be self working between a collapsed state, when said catheter apparatus moves upwards in said urethra towards the bladder, and an expanded state permitted by said urethra and opposing to any downward movement of the tube assembly.

6. The catheter apparatus according to claim 5, comprising said another expandable member, which comprises flexible second tongues distributed about said distal tube section, each of said tongues being arranged to be elastically biased towards a radial and outward position.

7. The catheter apparatus according to claim 6, wherein when the second tongues are in said radial and outward position, each of said second tongue extends obliquely with respect to the longitudinal axis towards a proximal end of said catheter apparatus.

8. The catheter apparatus according to claim 5, wherein said connector of said tube assembly connects to the open proximal end of said distal tube section at a point of attachment located adjacent to said another expandable member and to the distal end of said proximal tube section at a point of attachment located adjacent and proximal to said expandable member of said proximal tube section.

9. A prostatic stent consisting of a tube assembly comprising:
- a distal tube section having a closed distal end and a open proximal end, said distal end including at least one orifice to enable urine from a bladder to enter the distal tube section and to flow into and through the distal tube section, across a connector and through a sphincter;
- a proximal tube section having a distal end and a proximal end; and
- an expandable member disposed on said proximal tube section comprising flexible tongues, each of said tongues being arranged to be elastically biased towards a radial and outward position so that a degree of the tongues opening adapts automatically to a variable diameter of a urethra during progression of the stent inside a lumen of the urethra and said tongues being permanently abutted in spread condition against a proximal side of the sphincter once said stent is in a correct position in order to oppose any upward movement of said stent in said urethra,
wherein said connector connects the open proximal end of said distal tube section and the distal end of said proximal tube section together; said connector being attached to said proximal tube section at a point of attachment situated proximal to the tongues of the expandable member of said proximal tube section, the connector having a length of approximately 36 mm.

10. The prostatic stent according to claim 9, further comprising a controller that comprises a sheath adapted to enclose said distal end of said proximal tube section and constrain all the tongues of the expandable member in a collapsed position lying in a longitudinal direction.

11. The prostatic stent according to claim 9, wherein when said tongues are at said radial and outward position, each tongue extends obliquely with respect to a longitudinal axis towards a distal end of said stent.

12. The prostatic stent according to claim 9, comprising another expandable member, which comprises flexible second tongues distributed about said distal tube section, each of said second tongues being arranged to be elastically biased towards a radial and outward position.

13. The prostatic stent according to claim 12, wherein when said second tongues are in said radial and outward position, each of said second tongue extends obliquely with respect to the longitudinal axis towards a proximal end of said stent.

14. The prostatic stent according to claim 12, wherein said connector connects to the open proximal end of said distal tube section at a point of attachment located adjacent to said another expandable member and to the distal end of said proximal tube section at a point of attachment located adjacent and proximal to said expandable member of said proximal tube section.

15. The prostatic stent according to claim 9, wherein said connector comprises threads distributed about a longitudinal axis of said stent, attached on opposite ends respectively to said open proximal end of said distal tube and said distal end of said proximal tube section.

* * * * *